(12) United States Patent
Yamamoto et al.

(10) Patent No.: US 7,876,432 B2
(45) Date of Patent: *Jan. 25, 2011

(54) METHOD FOR DETECTING POSITION OF DEFECT ON SEMICONDUCTOR WAFER

(75) Inventors: Masayuki Yamamoto, Ibaraki (JP);
Satoshi Ikeda, Kameyama (JP)

(73) Assignee: Nitto Denko Corporation, Osaka (JP)

( * ) Notice: Subject to any disclaimer, the term of this patent is extended or adjusted under 35 U.S.C. 154(b) by 268 days.

This patent is subject to a terminal disclaimer.

(21) Appl. No.: 12/166,037

(22) Filed: Jul. 1, 2008

(65) Prior Publication Data
US 2009/0009755 A1    Jan. 8, 2009

(30) Foreign Application Priority Data
Jul. 2, 2007    (JP) .............................. 2007-174111

(51) Int. Cl.
*G01N 21/00*    (2006.01)

(52) U.S. Cl. ................................................. 356/237.5

(58) Field of Classification Search ....................... None
See application file for complete search history.

(56) References Cited

U.S. PATENT DOCUMENTS
2005/0062960 A1*   3/2005   Tsuji et al. ............... 356/237.2

FOREIGN PATENT DOCUMENTS
JP    08-279547 A    10/1996
JP    2003-258062 A   9/2003

* cited by examiner

*Primary Examiner*—Gregory J Toatley
*Assistant Examiner*—Amanda H Merlino
(74) *Attorney, Agent, or Firm*—Cheng Law Group, PLLC (57) ABSTRACT

A method of this invention involves: detecting a shape of an outer periphery of a semiconductor wafer with a first detecting device; determining a center position of the semiconductor wafer based on a detected result by the first detecting device; receiving a light beam reflected from a surface of the semiconductor wafer with a second detecting device; detecting an alignment part based on a detected result by the second detecting device to determine a position of the alignment part; and detecting a defect based on the detected result by the second detecting device to determine a position of the defect.

8 Claims, 6 Drawing Sheets

METHOD FOR DETECTING POSITION OF DEFECT ON SEMICONDUCTOR WAFER

BACKGROUND OF THE INVENTION (1) Field of the Invention

The present invention relates to a method for detecting a position of a defect such as chipping or cracking that occurs at an outer periphery of a semiconductor wafer.

(2) Description of the Related Art

In order to detect a center position of a semiconductor wafer, conventionally, there has been utilized a detecting device of a light transmission type. The detecting device includes a light projector and a light receiver disposed so as to be opposed to each other with a peripheral edge of the semiconductor wafer being placed therebetween. Specifically, the detecting device detects an alignment part such as a notch or an orientation flat formed at the peripheral edge of the semiconductor wafer. As a method for obtaining the center position of the semiconductor wafer on the basis of the detected position, there has been known a detecting method of a light transmission type (refer to, for example, JP-A 08-279547).

There has been also known a detecting method of a light reflection type. This method involves: receiving, at an image capturing camera, a light beam which is emitted to a surface of a semiconductor wafer and, then, is reflected from the surface of the semiconductor wafer; and determining a position of a notch on the basis of data of images captured by the image capturing camera (refer to, for example, JP-A 2003-258062).

However, the detecting method of the light transmission type has the following problems. In a case where a protective tape is joined to a pattern formation side of a semiconductor wafer, a metal film is deposited on or dust is attached to the protective tape at a portion corresponding to the notch in a previous process. Consequently, a light transmittance is lowered at the notch, so that the notch cannot be detected with accuracy.

On the other hand, the detecting method of the light reflection type has the following problems. A light beam emitted to a surface of a semiconductor wafer is reflected irregularly in some cases depending on a state of the surface of the semiconductor wafer. An image of a notch becomes blurred due to an influence of the irregular reflection, so that the notch cannot be detected with accuracy. According to the conventional method, particularly, a portion corresponding to a semiconductor wafer is represented in black and a remaining portion is represented in white in data of a captured image.

Accordingly, there is a problem that a defect such as minute chipping smaller than a notch or cracking on a surface of a semiconductor wafer cannot be detected.

SUMMARY OF THE INVENTION

A principal object of the present invention is to provide a method capable of detecting, with good accuracy, a defect such as minute chipping smaller than a notch or cracking on a surface of a semiconductor wafer.

In order to achieve this object, the present invention adopts the following configuration:

A method for detecting a position of a defect on a semiconductor wafer, comprising the steps of:

detecting a shape of an outer periphery of a semiconductor wafer with a first detecting device;

determining a center position of the semiconductor wafer based on a result of the detection by the first detecting device;

receiving a light beam reflected from a surface of the semiconductor wafer with a second detecting device;

detecting an alignment part based on a detected result by the second detecting device to determine a position of the alignment part; and detecting a defect based on the detected result by the second detecting device to determine a position of the defect.

The method according to the present invention is implemented as follows. That is, this method involves: detecting a shape of an outer periphery of a semiconductor wafer with a first detecting device (hereinafter, appropriately referred to as a "wafer"); detecting a position of an alignment part such as a notch or an orientation flat formed at an outer periphery of the wafer; and determining a center position of the wafer on the basis of a result of the detection. In this case, the first detecting device may be of a light transmission type or a light reflection type.

This method also involves: receiving with a second detecting device a light beam reflected from a pattern formation side, that is, a front face or a back face of the wafer; and detecting the alignment part on the outer periphery of the wafer to determine the position of the alignment part and detecting a defect on the basis of a result of the detection by the second detecting device to determine a position of the defect.

A memory or the like stores position information obtained as described above. Thus, the position information can be utilized as information for aligning a semiconductor wafer and setting a direction of the semiconductor wafer at the time of mounting the semiconductor wafer on a processing stage in a subsequent process.

In this method, preferably, the step of receiving the reflected light beam includes, for example, guiding the light beam to an imaging device through an optical member disposed on an optical path of the light beam, the light beam being emitted perpendicularly to the semiconductor wafer and then reflected perpendicularly from the surface of the semiconductor wafer.

Also in this method, preferably, the optical member is a beam splitter, emission light beam transmitting the beam splitter is totally reflected on a back face of the semiconductor wafer, the reflected light beam passes back to the optical path identical to the emission optical path, the reflected light beam is reflected orthogonally to the optical path during transmitting the beam splitter, and consequently the reflected light beam is guided to the imaging device disposed in a direction orthogonal to the optical path.

According to this method, since a light beam is emitted perpendicularly to a semiconductor wafer, irregular reflection can be suppressed irrespective of characteristics of a surface of the semiconductor wafer. As a result, minute cracking on the surface irradiated with the light beam can be detected with good accuracy.

In this method, a position of a defect can be determined as follows.

(1) The position of the defect is determined as an amount of deviation from the alignment part serving as a reference position in a circumferential direction of the semiconductor wafer.

(2) The position of the defect is determined by pattern matching of image data about an outer periphery of the semiconductor wafer acquired by the imaging device with reference image data acquired in advance.

(3) The position of the defect is determined by estimating a candidate of the defect on the basis of a comparison of an area obtained from the image data about the outer periphery of the semiconductor wafer acquired by the imagine device and a reference area obtained in advance, capturing an image of the estimated portion again with the imaging device, and performing pattern matching of the acquired image data with the reference image data acquired in advance in order to identify a position of the defect.

As described above, chipping or cracking that occurs at a peripheral edge of a wafer can be determined with good accuracy from an amount of deviation from an alignment part such as a notch or an orientation flat in a circumferential direction of the wafer.

This method may further comprise the step of determining a direction of joining an adhesive tape to the semiconductor wafer on the basis of position information of the defect.

According to this method, in a case of joining an adhesive tape to a semiconductor wafer in such a manner that a joining roller rolls on the semiconductor wafer, the adhesive tape can be joined in a direction of preventing a defect such as cracking from becoming further deteriorated due to a pressing force and movement of the joining roller.

This method may further comprise the steps of joining a protective tape to a pattern formation side of the semiconductor wafer; and determining a direction of separating the protective tape from the semiconductor wafer on the basis of position information of the defect.

According to this method, in a case of separating a protective tape from a semiconductor wafer in such a manner that a separating roller or an edge member moves on the semiconductor wafer, the protective tape can be separated from the semiconductor wafer in a direction of preventing a defect such as cracking from becoming further deteriorated due to a pressing force and movement of the separating roller or the like.

This method may further comprise the step of sending position information of the defect on the semiconductor wafer to a subsequent process.

According to this method, position information of a defect on a semiconductor wafer is utilized in a subsequent process, leading to prevention of further deterioration of the defect such as cracking.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Hereinafter, description will be given of one embodiment of the present invention with reference to the drawings.

Figure 1:
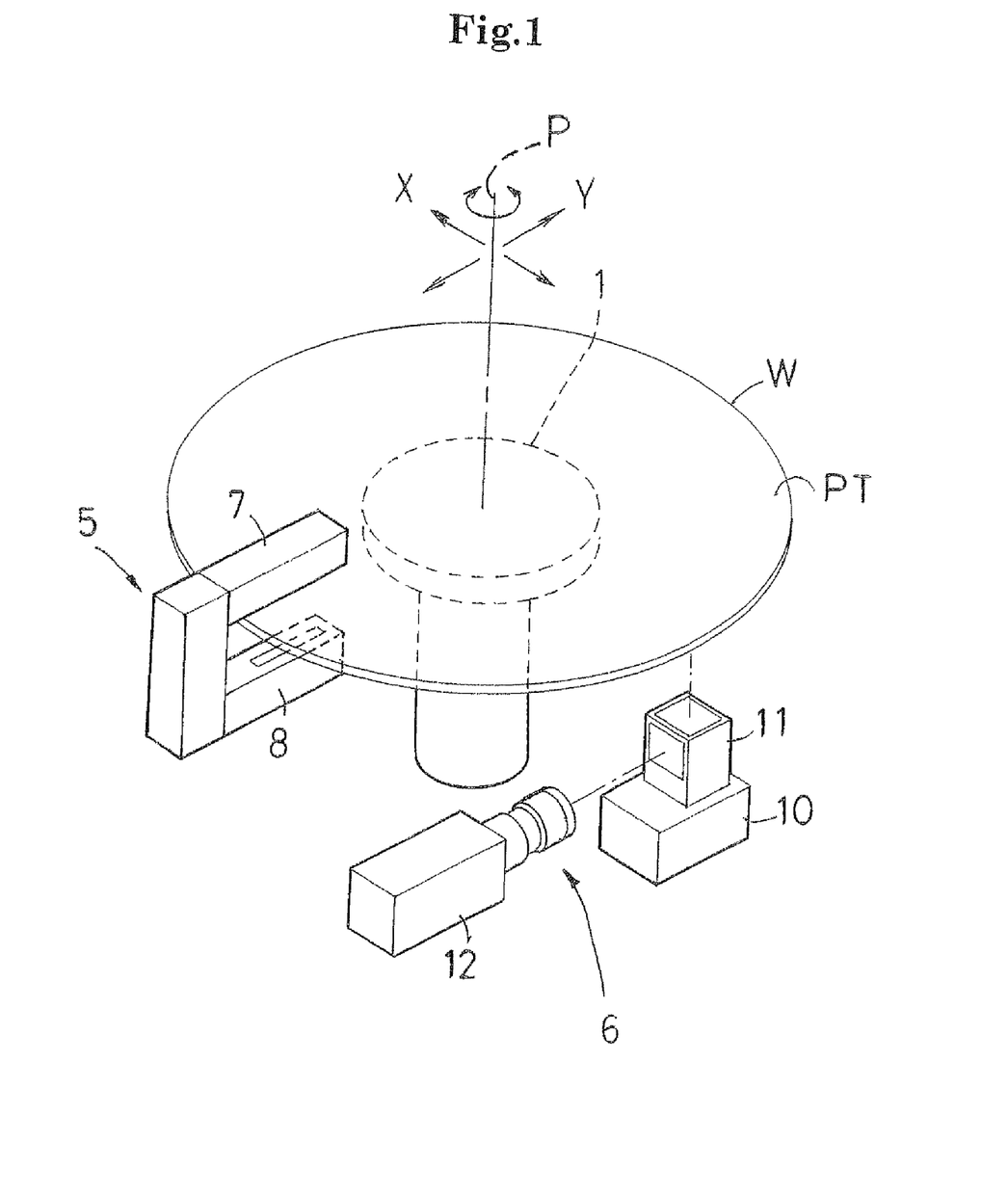
FIG. 1 is a perspective view showing main components of an aligner.
Figure 2:
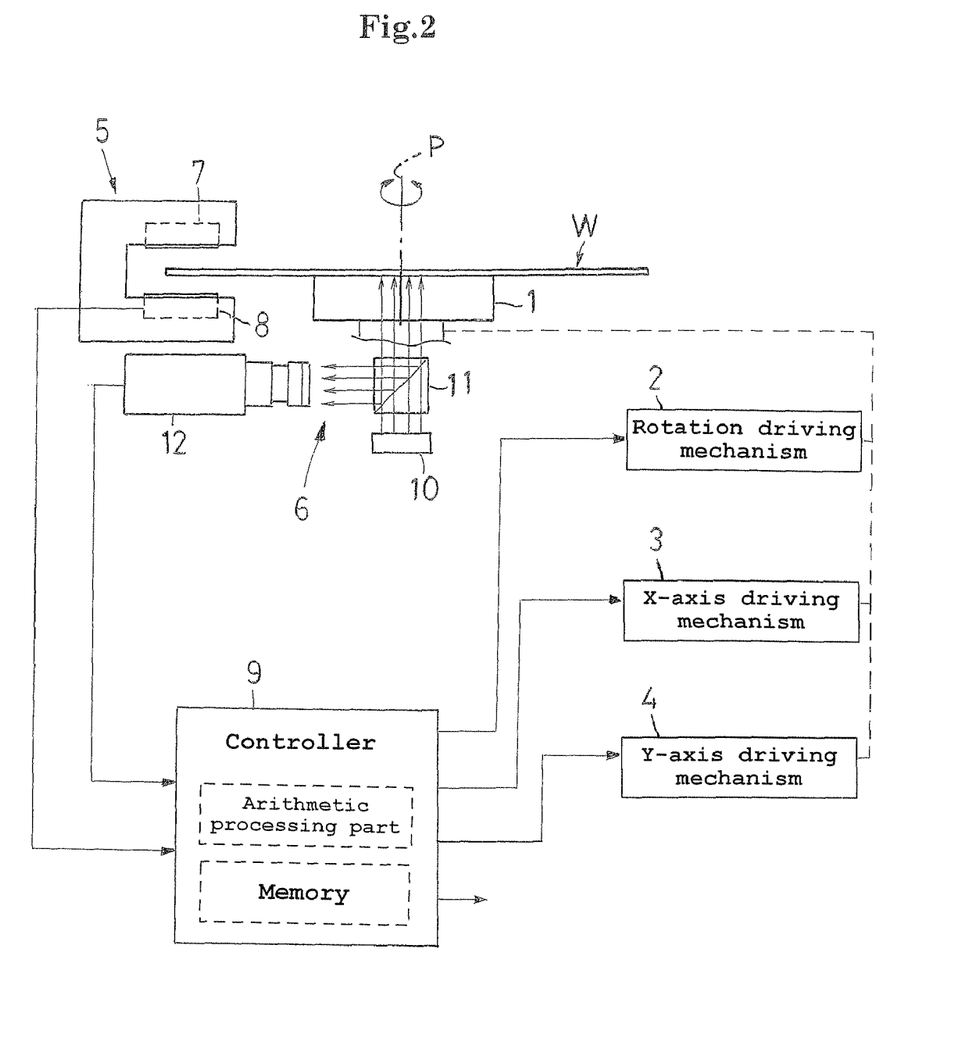
FIG. 2 shows a linkup in the aligner.
Figure 5:
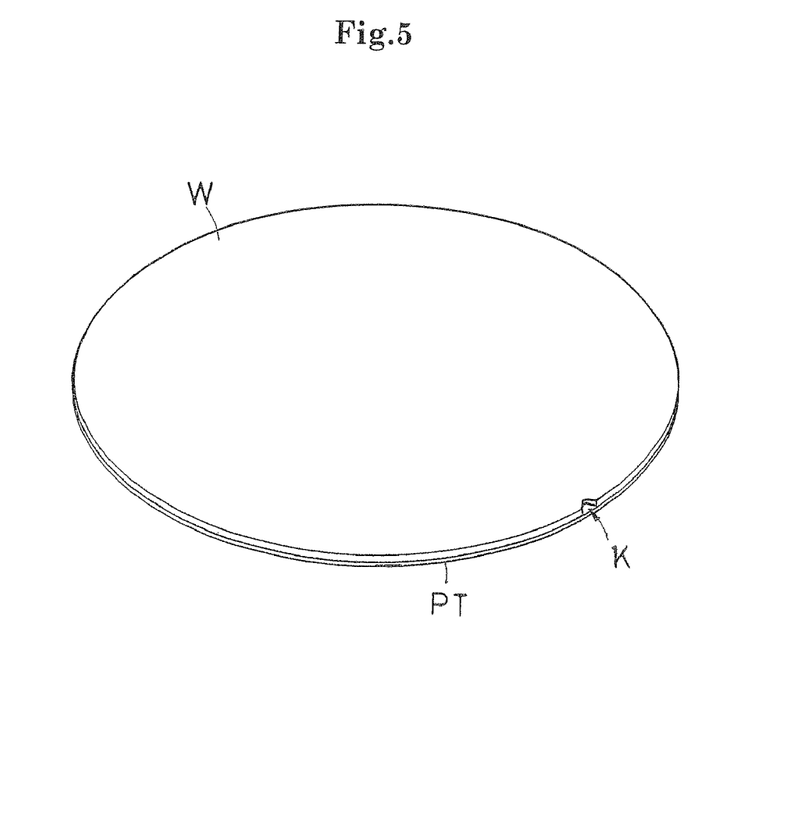
FIG. 5 is a perspective view showing a back face of the semiconductor wafer.
Figure 6:
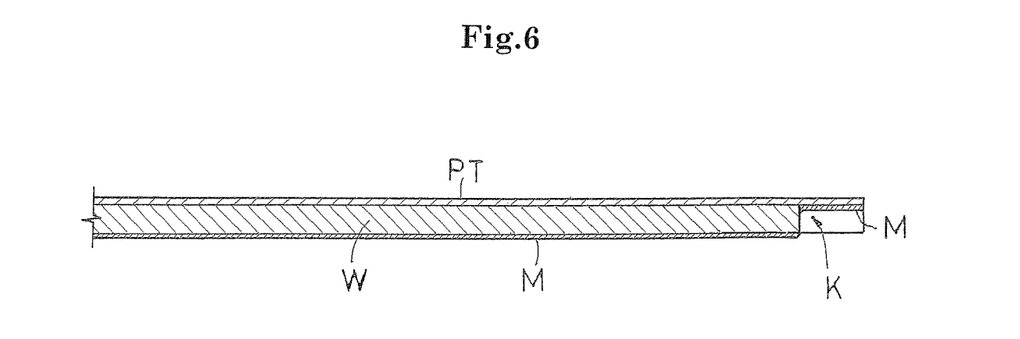
FIG. 6 is an enlarged sectional view showing a notch of the semiconductor wafer.

FIG. 1 is a perspective view showing main components of an aligner for use in alignment of a semiconductor wafer (hereinafter, simply referred to as a wafer) W. FIG. 2 shows a linkup in the aligner. FIG. 5 is a perspective view showing a back face of the wafer W to be subjected to processes. FIG. 6 is a sectional view partially showing the wafer W.

As shown in FIGS. 5 and 6, the wafer W has a front face on which a circuit pattern is formed, and a protective tape PT is joined to the front face. In this state, a back face of the wafer W is subjected to grinding, and then a metal layer M is deposited on the back face. Accordingly, the metal layer M is also deposited on the bared protective tape PT at a portion corresponding to a notch K formed as an alignment part at an outer periphery of the wafer W.

As shown in FIGS. 1 and 2, the aligner is rotatable about a vertical axis center P by means of a rotation driving mechanism 2 such as a pulse motor. The aligner is provided with an aligner stage 1 movable horizontally in an X-axis direction and a Y-axis direction, which are orthogonal to each other, by means of an X-axis driving mechanism 3 and a Y-axis driving mechanism 4. The wafer W is sucked on the aligner stage 1 with the front face protected by the protective tape PT being directed upward, and the aligner stage 1 suction-holds the wafer W.

A peripheral edge measuring mechanism 5 of a light transmission type, which serves as a first detecting device, is provided at a predetermined position of the aligner stage 1 in a circumferential direction. A defect detecting mechanism 6 of a light reflection type, which serves as a second detecting device, is provided at another predetermined position of the aligner stage 1 in the circumferential direction.

The peripheral edge measuring mechanism 5 includes a light source 7 and a light receiving sensor 8. The light source 7 emits a light beam to the wafer W from above. The light receiving sensor 8 is provided below the wafer W so as to be opposed to the light source 7. The light receiving sensor 8 to be used herein is a CCD line sensor that includes a large number of light receiving elements arranged linearly in a radial direction of the wafer W. The light receiving sensor 8 acquires detection data, and a controller 9 that incorporates a microcomputer receives the detection data.

The defect detecting mechanism 6 includes a light source 10, a polarized beam splitter 11 and a CCD camera 12. The light source 10 emits a light beam perpendicularly to the back face of the wafer W (in a down-to-up direction in FIG. 1). The polarized beam splitter 11 totally reflects the light beam from the light source 10 perpendicularly on the back face of the wafer W such that the light beam passes a return optical path identical to an emission light path, and changes a direction of the reflected light beam perpendicularly (a leftward direction in FIG. 1). The CCD camera 12 receives the reflected light beam guided horizontally by the polarized beam splitter 11. The controller 9 includes a storing device such as memory that stores data of an image captured by the CCD camera 12.

The aligner is configured as described above. With reference to flowcharts in FIGS. 3 and 4, next, description will be given of a wafer aligning process and a defect detecting process each executed with the use of the aligner.

Figure 3:
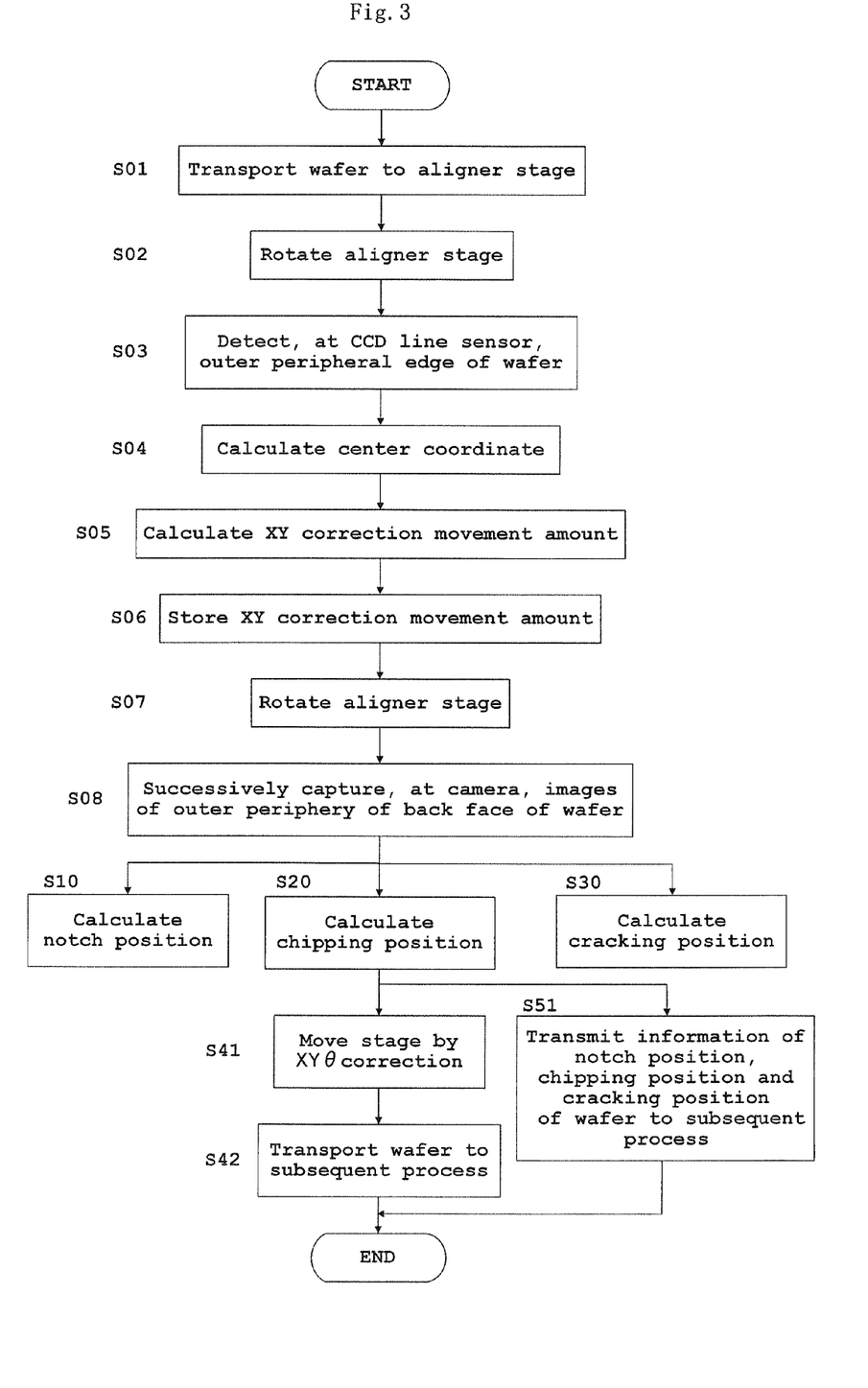
FIG. 3 is a flowchart entirely showing a procedure of processes for a semiconductor wafer.

First, an appropriate handling device such as a robot arm places the wafer W on the aligner stage 1 with the front face having the protective tape PT joined thereto being directed upward. The aligner stage 1 suction-holds the wafer W placed thereon (step S01).

Next, the rotation driving mechanism 2 allows the aligner stage 1 to rotate by 360° at a predetermined speed in a predetermined direction (step S02). Simultaneously, the light receiving sensor (the CCD line sensor) 8 of the peripheral edge measuring mechanism 5 detects the outer peripheral edge of the wafer W to measure and store a position of the outer peripheral edge at each rotational phase (step S03).

The controller 9 calculates a center position of the wafer W as a coordinate position (a center coordinate) on an XY coordinate, on the basis of the measured and stored data (step S04).

The controller 9 also calculates, as an XY correction movement amount, a deviation of the center coordinate of the wafer W from the center of the aligner stage 1 (step S05). The storing device such as the memory in the controller 9 stores this correction movement amount (step S06).

Next, the rotation driving mechanism 2 allows the aligner stage 1 to rotate at the predetermined speed (step S07). Herein, the light source 10 emits a light beam to the back face (the bottom side) of the outer periphery of the wafer W, and the CCD camera 12 successively captures images of the light beam which is reflected totally from the back face of the wafer W and passes the return optical path identical to the emission optical path. The memory or the like in the controller 9 stores data of the captured image (step S08). An arithmetic processing part in the controller 9 executes a notch position calculating process (step S10), a chipping position calculating process (step S20) and a cracking position calculating process (step S30) in parallel, on the basis of the acquired image data. With reference to the flowchart in FIG. 4, next, description will be given of the respective calculating processes.

Figure 4:
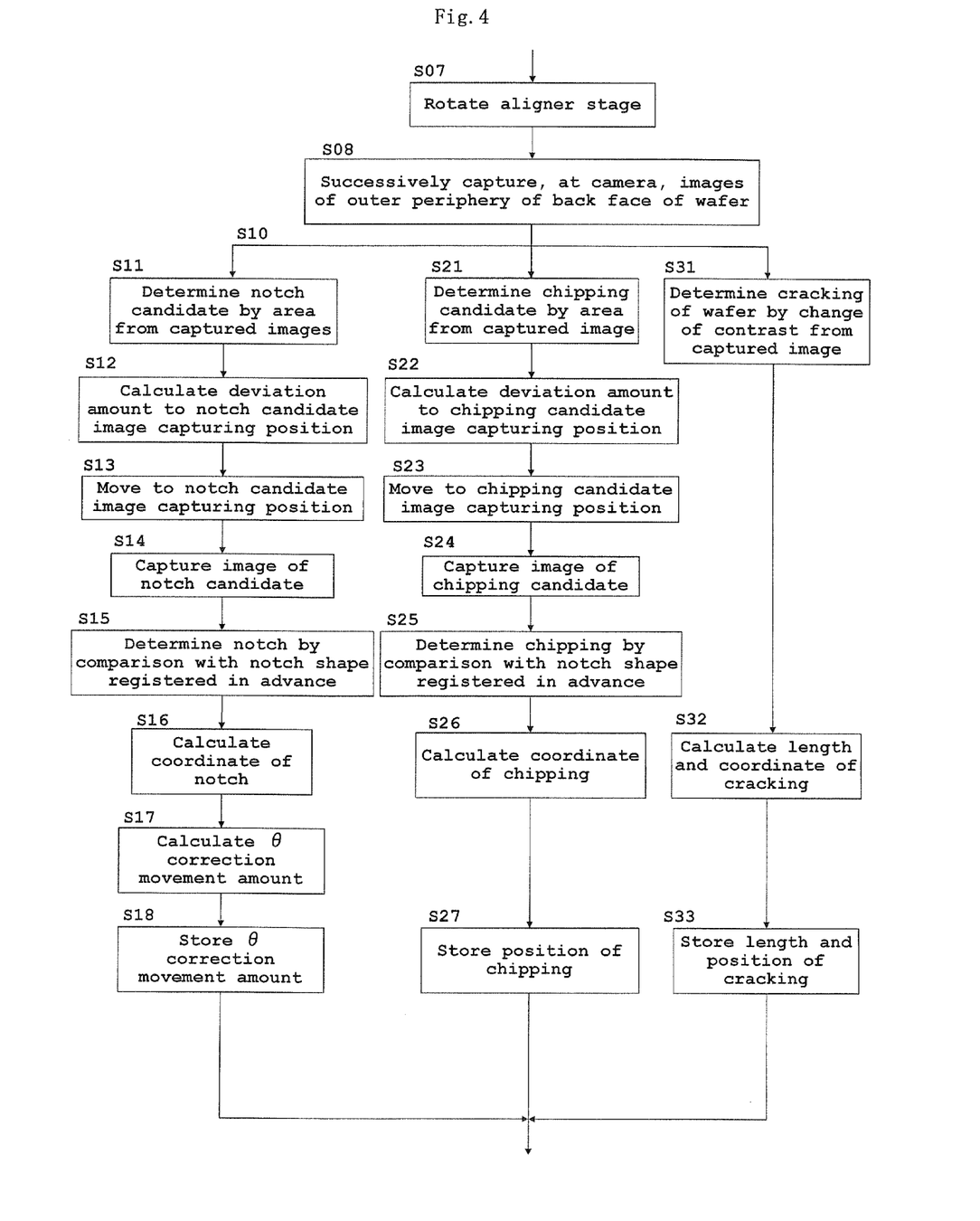
FIG. 4 is a flowchart partially showing the procedure of processes.

<Notch Position Calculating Process (Step S10)>

The arithmetic processing part determines a candidate supposed as the notch K as a coincident portion by an area comparison from the images successively captured by the CCD camera 12 (step S11). The image utilized herein is obtained by reception of a substantially total amount of the light beam that is emitted from the light source 10 and is reflected from the back face of the wafer W. Accordingly, the normal portion of the back face of the wafer W is highlighted in white. On the other hand, the notch, the chipping and the cracking on the outer peripheral edge of the wafer W as well as the outer peripheral region of the wafer W are represented in black.

Next, the arithmetic processing part calculates a deviation amount (an angle of rotation) from an image capturing start position to a position of the notch candidate (step S12). On the basis of a result of the calculation, the rotation driving mechanism 2 allows the aligner stage 1 to rotate by the deviation amount such that the notch candidate is aligned with an image capturing position (step S13).

When the notch candidate is aligned with the image capturing position, the CCD camera 12 captures an image of the notch candidate again (step S14). Then, the arithmetic processing part compares the notch candidate with a notch shape registered in advance by pattern matching or the like to determine the notch K (step S15).

When the notch K is determined, the arithmetic processing part calculates a coordinate of a position of the notch K (step S16). On the basis of this coordinate data, the arithmetic processing part calculates a correction movement amount θ for moving the notch K to a preset reference position (a rotational phase) (step S17). Then, the memory or the like in the controller 9 stores the correction movement amount θ (step S18).

<Chipping Position Calculating Process (Step S20)>

The arithmetic processing part determines a candidate supposed as chipping by an area comparison from the images successively captured by the CCD camera 12 (step S21).

Next, the arithmetic processing part calculates a deviation amount (an angle of rotation) from the image capturing start position to a position of the chipping candidate (step S22). On the basis of a result of the calculation, the rotation driving mechanism 2 allows the aligner stage 1 to rotate by the deviation amount such that the chipping candidate is aligned with the image capturing position (step S23).

When the chipping candidate is aligned with the image capturing position, the CCD camera 12 captures an image of the chipping candidate again (step S24). Then, the arithmetic processing part compares the chipping candidate with the notch shape registered in advance by pattern matching or the like to determine the chipping from a result of the pattern matching (step S25).

When the chipping is determined, the arithmetic processing part calculates a coordinate of a position of the chipping (step S26). Then, the memory or the like in the controller 9 stores the coordinate (step S27).

<Cracking Position Calculating Process (Step S30)>

The arithmetic processing part determines cracking on the wafer W by a change of contrast from the images successively captured by the CCD camera 12 (step S31). The image utilized herein is obtained by reception of a substantially total amount of the light beam emitted from the light source 10 and then reflected from the back face of the wafer W. Accordingly, the normal portion of the back face of the wafer W is highlighted in white. On the other hand, the notch, the chipping and the cracking on the outer peripheral edge of the wafer W as well as the outer peripheral region of the wafer W are represented in black. That is, an influence of irregular reflection caused by characteristics of the back face of the wafer W is eliminated, so that the minute cracking is displayed clearly on the image of the back face of the wafer W represented in white.

When the cracking on the wafer W is determined, the arithmetic processing part calculates a length and a coordinate position of the cracking (step S32). Then, the memory or the like in the controller 9 stores a result of the calculation (step S33).

After completion of the processes described above, the arithmetic processing part executes a wafer aligning process and a detection information transmitting process.

In the wafer aligning process, the rotation driving mechanism 2 allows the aligner stage 1 to move horizontally on the X-Y plane shown in FIG. 1, on the basis of the XY correction movement amount stored in the memory or the like. Simultaneously, the rotation driving mechanism 2 allows the aligner stage 1 to rotate on the basis of the correction movement amount θ. As a result, the wafer W is corrected such that the center position is aligned with the reference position and the notch K is directed to the reference rotational phase in a predetermined posture (step S41). Thereafter, the wafer W is transported from the aligner stage 1 to a subsequent process (step S42).

In the detection information transmitting process, detection information such as the position of the notch, the position of the chipping on the wafer, and the position of the cracking on the wafer are transmitted to each controller in each process through a network or a recording medium. Alternatively, a label having the position information recorded therein while being coded two-dimensionally or three-dimensionally is attached to the wafer W (step S51).

Next, description will be given of one example of a process in a case where chipping or cracking on a wafer W is detected.

Figure 7:
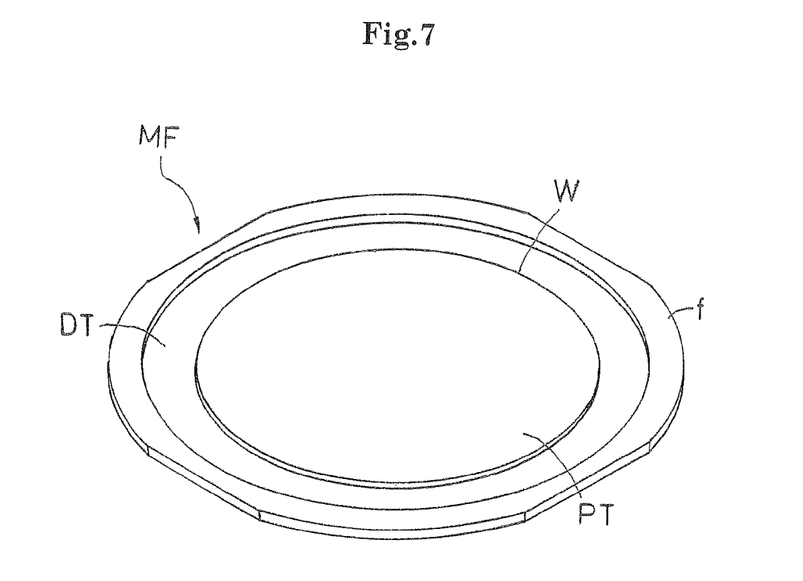
FIG. 7 is a perspective view showing a mount frame.

A wafer W subjected to back grinding is attached to and held by a ring frame f through a dicing tape DT; thus, a mount frame MF shown in FIG. 7 is prepared. In this case, the position information transmitted from the previous process is utilized.

If the wafer W has chipping or cracking detected at a region corresponding to the outer periphery of the circuit pattern, the position information of the chipping or the like is read by the controller in each process. On the basis of this position information, the portion having no chipping or cracking is set as a tape joining direction. For example, the tape joining direction (a joining roller moving direction) is set such that the chipping or the cracking is located at a tape joining termination end side. That is, the chipped portions are compared with each other, and a position of the larger one is preferentially set as the tape joining termination end side. Alternatively, the tape joining direction is set along a longitudinal direction of the cracking. The setting of the tape joining direction allows reduction of a tape joining stress to be applied to the wafer W, leading to prevention of further deterioration of the chipping and the cracking.

Figure 8:
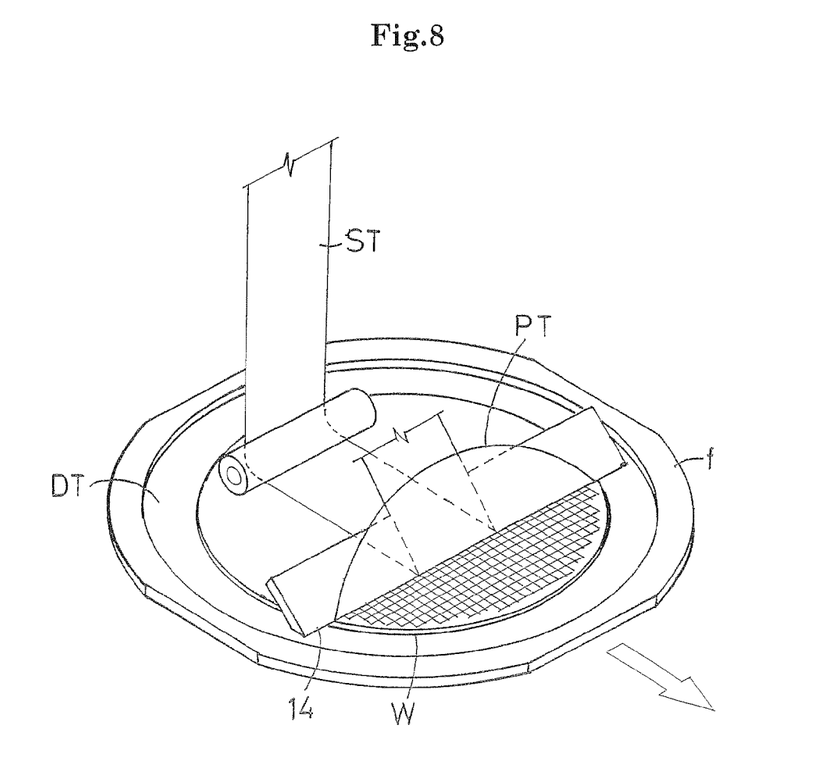
FIG. 8 is a perspective view showing a protective tape separating process.

In order to attach the wafer W to the ring frame f through the dicing tape DT and, then, separate the protective tape PT from the front face of the wafer W, the following process is executed. As shown in FIG. 8, for example, a separating tape ST having a narrow width is joined to the protective tape PT by an edge member 14 and, almost simultaneously, is folded back and collected with the use of a tip end of the edge member 14. Thus, the protective tape PT can be separated together with the separating tape ST from the front face of the wafer W.

In this separating process, if chipping or cracking is detected on the wafer W, a portion having no chipping or cracking is set as a tape separating direction as in the case of joining of the dicing tape DT. That is, the joining direction of the separating tape ST (the moving direction of the edge member 14) is set such that the chipping or the cracking is located at the tape joining termination end side. The joining of the separating tape ST allows reduction of a tape separating stress and a pressing force of the edge member 14 each applied to the chipping or the like on the wafer W and reduction of a separating stress generated upon separation of the separating tape ST (i.e., suppression of a degree of warpage).

For example, in a case where the chipping is located at the separation termination end position, even when warpage starting from the position of the chipping occurs in the separating direction, the wafer W is not damaged from the chipping thereafter. Accordingly, it is possible to prevent further deterioration of chipping or cracking of the wafer W upon separation of the separating tape ST.

In a case of occurring the cracking, if the longitudinal direction of the cracking is coincide with a separation contact, the wafer W is readily bent from the cracking due to the separating stress. However, the separation of the protective tape PT in the longitudinal direction allows prevention of such a disadvantage. Moreover, the separation starting from the center of the longitudinal cracking in a radial direction (outward) allows suppression of a degree of warpage of the wafer W upon separation of the separating tape ST and prevention of further deterioration of the cracking.

The present invention is not particularly limited to the embodiment described above, and may be modified as follows.

(1) In the foregoing embodiment, the first detecting device 5 that utilizes the CCD line sensor 8 determines the center position of the wafer W. However, the center position of the wafer W may be determined by an imaging process using a CCD camera.

(2) In the foregoing embodiment, the notch position calculating process, the chipping position calculating process and the cracking position calculating processes are executed in parallel. However, these processes may be executed in sequence.

(3) In the foregoing embodiment, the light beam is emitted perpendicularly to the back face of the wafer W. However, the light beam may be emitted to the front face having a circuit pattern formed thereon.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method for detecting a position of a defect on a semiconductor wafer, comprising the steps of:
    detecting, at a first detecting device, an outer peripheral shape of a semi-conductor wafer with a sensor while rotating the semiconductor wafer placed on an alignment stage;
    determining a center position of the semiconductor wafer from an amount of deviation of the center position with respect to a center of the alignment stage on the basis of a result of the detection by the first detecting device;
    emitting a light beam perpendicularly to the semiconductor wafer, emission light beam transmitting the beam splitter being totally reflected on a back face of the semiconductor wafer, the reflected light beam passing back to a optical path identical to the emission optical path, the reflected light beam being reflected orthogonally to the optical path during transmitting the beam splitter, and consequently the reflected light beam being detected by an imaging device disposed on the optical path;
    detecting an alignment part on the basis of a result of the detection by the imaging device in order to determine a position of the alignment part;
    estimating a candidate of the defect based on a comparison of an area obtained from the image data about the outer periphery of the semiconductor wafer acquired by the imaging device and a reference area obtained in advance, capturing again an image of the estimated portion with the imaging device, and performing pattern matching of the acquired image data with the reference image data acquired in advance to determine the defect position; and
    determining a direction of joining an adhesive tape to the semiconductor wafer based on information of the defect position.

2. The method according to claim 1, further comprising the step of:
    sending position information of the defect on the semiconductor wafer to a subsequent process.

3. A method for detecting a position of a defect on a semiconductor wafer, comprising the steps of:
    detecting, at a first detecting device, an outer peripheral shape of a semi-conductor wafer with a sensor while rotating the semiconductor wafer placed on an alignment stage;
    determining a center position of the semiconductor wafer from an amount of deviation of the center position with respect to a center of the alignment stage on the basis of a result of the detection by the first detecting device;
    emitting a light beam perpendicularly to the semiconductor wafer, emission light beam transmitting the beam splitter being totally reflected on a back face of the semiconductor wafer, the reflected light beam passing back to a optical path identical to the emission optical path, the reflected light beam being reflected orthogonally to the optical path during transmitting the beam splitter, and consequently the reflected light beam being detected by an imaging device disposed on the optical path;

detecting an alignment part on the basis of a result of the detection by the imaging device in order to determine a position of the alignment part;

estimating a candidate of the defect based on a comparison of an area obtained from the image data about the outer periphery of the semiconductor wafer acquired by the imaging device and a reference area obtained in advance, capturing again an image of the estimated portion with the imaging device, and performing pattern matching of the acquired image data with the reference image data acquired in advance to determine the defect position; and determining a direction of separating a protective tape from the semiconductor wafer based on the information of the defect position, the semiconductor wafer having the protective tape joined to the pattern formation side thereof.

4. The method according to claim 3, further comprising the step of:

sending position information of the defect on the semiconductor wafer to a subsequent process.

5. A method for detecting a position of a defect on a semiconductor wafer, comprising the steps of:

detecting, at a first detecting device, an outer peripheral shape of a semi-conductor wafer with a sensor while rotating the semiconductor wafer placed on an alignment stage;

determining a center position of the semiconductor wafer from an amount of deviation of the center position with respect to a center of the alignment stage on the basis of a result of the detection by the first detecting device;

emitting a light beam perpendicularly to the semiconductor wafer, emission light beam transmitting the beam splitter being totally reflected on a back face of the semiconductor wafer, the reflected light beam passing back to a optical path identical to the emission optical path, the reflected light beam being reflected orthogonally to the optical path during transmitting the beam splitter, and consequently the reflected light beam being detected by an imaging device disposed on the optical path;

detecting an alignment part on the basis of a result of the detection by the imaging device in order to determine a position of the alignment part;

estimating a candidate of the defect based on a comparison of an area obtained from the image data about the outer periphery of the semiconductor wafer acquired by the imaging device and a reference area obtained in advance, capturing again an image of the estimated portion with the imaging device, and determining the defect position by an amount of deviation from the alignment part serving as a reference position in a circumferential direction of the semiconductor wafer; and determining a direction of joining an adhesive tape to the semiconductor wafer based on information of the defect position.

6. The method according to claim 5, further comprising the step of:

sending position information of the defect on the semiconductor wafer to a subsequent process.

7. A method for detecting a position of a defect on a semiconductor wafer, comprising the steps of:

detecting, at a first detecting device, an outer peripheral shape of a semi-conductor wafer with a sensor while rotating the semiconductor wafer placed on an alignment stage;

determining a center position of the semiconductor wafer from an amount of deviation of the center position with respect to a center of the alignment stage on the basis of a result of the detection by the first detecting device;

emitting a light beam perpendicularly to the semiconductor water, emission light beam transmitting the beam splitter being totally reflected on a back face of the semiconductor wafer, the reflected light beam passing back to a optical path identical to the emission optical path, the reflected light beam being reflected orthogonally to the optical path during transmitting the beam splitter, and consequently the reflected light beam being detected by an imaging device disposed on the optical path;

detecting an alignment part on the basis of a result of the detection by the imaging device in order to determine a position of the alignment part;

estimating a candidate of the defect based on a comparison of an area obtained from the image data about the outer periphery of the semiconductor wafer acquired by the imaging device and a reference area obtained in advance, capturing again an image of the estimated portion with the imaging device, and determining the defect position by an amount of deviation from the alignment part serving as a reference position in a circumferential direction of the semiconductor wafer; and determining a direction of separating a protective tape from the semiconductor wafer based on the information of the defect position, the semiconductor wafer having the protective tape joined to the pattern formation side thereof.

8. The method according to claim 7, further comprising the step of:

sending position information of the defect on the semiconductor wafer to a subsequent process.

* * * * *